United States Patent
Ashfaque

(10) Patent No.: US 9,682,215 B2
(45) Date of Patent: Jun. 20, 2017

(54) TWO-PART CANNULA DRESSING

(71) Applicant: BENEDETTI INTERNATIONAL LIMITED, Wishaw (GB)

(72) Inventor: Muhammad Ashfaque, Kent (GB)

(73) Assignee: BENEDETTI INTERNATIONAL LIMITED, Wishaw (GB)

(*) Notice: Subject to any disclaimer, the term of this patent is extended or adjusted under 35 U.S.C. 154(b) by 249 days.

(21) Appl. No.: 14/378,136

(22) PCT Filed: Feb. 11, 2013

(86) PCT No.: PCT/GB2013/050302
§ 371 (c)(1),
(2) Date: Aug. 12, 2014

(87) PCT Pub. No.: WO2013/121182
PCT Pub. Date: Aug. 22, 2013

(65) Prior Publication Data
US 2015/0032057 A1    Jan. 29, 2015

(30) Foreign Application Priority Data

Feb. 13, 2012 (GB) ................................. 1202388.3
Nov. 7, 2012 (GB) ................................. 1220024.2

(51) Int. Cl.
*A61M 5/32* (2006.01)
*A61M 25/02* (2006.01)
*A61M 25/00* (2006.01)

(52) U.S. Cl.
CPC ..... *A61M 25/02* (2013.01); *A61M 2025/0008* (2013.01); *A61M 2025/0273* (2013.01); *A61M 2205/60* (2013.01)

(58) Field of Classification Search
CPC .......... A61M 25/02; A61M 2025/0273; A61M 2025/0246; A61M 2025/0253;
(Continued)

(56) References Cited

U.S. PATENT DOCUMENTS 4,324,237 A    4/1982  Buttaravoli
4,614,183 A *  9/1986  McCracken .......... A61F 13/023
                                                    128/846
(Continued)

FOREIGN PATENT DOCUMENTS

DE    202006005966 U1    10/2006
EP        0284219 A2     9/1988
(Continued)

OTHER PUBLICATIONS

Przykutta, Andreas, "International Search Report," prepared for PCT/GB2013/050302, as mailed Apr. 11, 2013, six pages.

*Primary Examiner* — Edelmira Bosques
*Assistant Examiner* — Leah Swanson
(74) *Attorney, Agent, or Firm* — Winstead PC

(57) ABSTRACT

The application relates to a two-part overlapping dressing for securing a cannula during intravenous catheterization on the skin surface of a patient. The dressing comprises a first flexible adhesive sheet (10) provided with an opening (16) spaced from all its peripheral edges; and a second flexible adhesive sheet (12). The opening (16) in the first sheet comprises a slit (18), one end of which terminates in an enlarged aperture (20). The second sheet (12) is dimensioned such that, when it is aligned with and adhered against the first sheet (10) in use, it is capable of overlapping the full length of the slit (18) so as to reduce the opening (16) to the size of the enlarged aperture (20). The apparatus allows for a more secure fitting of the cannula while minimizing the risk of infection.

23 Claims, 8 Drawing Sheets

(58) Field of Classification Search
CPC .. A61M 2025/0266; A61M 2025/0206; A61M 2025/024; A61F 2013/00412; A61F 2013/0421; A61F 2013/00655; A61F 2013/008; A61F 2013/00808; A61F 2013/00817; A61F 2013/00821; A61F 13/0259; Y10S 128/26
USPC ........ 604/180, 174; 128/887; 602/52, 54, 57
See application file for complete search history.

(56) References Cited

U.S. PATENT DOCUMENTS

| | | | |
|---|---|---|---|
| 4,941,882 A | 7/1990 | Ward et al. | |
| 5,282,791 A | 2/1994 | Lipton et al. | |
| 5,968,000 A | 10/1999 | Harrison et al. | |
| 2007/0078400 A1* | 4/2007 | Gesler, III | A61M 25/02 604/177 |
| 2010/0121282 A1* | 5/2010 | Propp | A61M 25/02 604/180 |
| 2010/0294286 A1* | 11/2010 | Bellamy | A61M 25/02 128/887 |

FOREIGN PATENT DOCUMENTS

| | | |
|---|---|---|
| EP | 2269548 A1 | 1/2011 |
| WO | WO-2004026389 A2 | 4/2004 |
| WO | WO-2011100181 A1 | 8/2011 |

\* cited by examiner

TWO-PART CANNULA DRESSING

The invention relates to a two-part dressing for securing a cannula during intravenous catheterization and to a method for securing a cannula on the skin surface of a patient.

BACKGROUND OF THE INVENTION

A catheterization procedure involves the piercing of a vein or artery of a patient with a needle carrying a cannula—also called "catheter"—and subsequently sliding the cannula over the needle and into the punctured blood vessel. After the needle is removed from the catheter, a tube—such as an IV line—is connected to the cannula via a connector for supplying an intravenous fluid to the patient.

Most catheterization procedures are carried out on cutaneous veins to minimize the health risks associated with any invasive procedure. One of the most frequent complications in catheterization procedures stems from repeated movements of the cannula inside the vein as well as the friction of the cannula against the entry site. This results in repeated micro-trauma and maceration of skin edges. This, in turn, contributes to conditions such as sore veins, phlebitis, infection and hence pain for the patient. Trauma can also be caused by accidental pulling of the connector and/or the attached IV line. These direct traumata, as well as multiple micro-traumas, to cutaneous veins will eventually damage the cutaneous veins to the extent that they are rendered unsuited for such procedures and may eventually result in more invasive procedures being needed such as central venous catheterization.

Repeated displacement of cannulas and consequent traumata lead to a requirement for re-siting, often multiple times. This may have a serious impact in term of material cost (e.g. needles, cannula and dressings) as well as additional clinician's time and detrimental effects on patient well-being.

Furthermore, the cannula poses a risk of infection and the entry site needs to be effectively protected from bacteria migrating from its connector to the puncture site along the length of the cannula.

Dressings adapted for catheterization are exemplified in patent documents such as EP0284219B2; U.S. Pat. No. 5,282,791; U.S. Pat. No. 5,968,000 and U.S. Pat. No. 4,941,882. Typically, these dressings comprise a slit or an indentation extending inwardly from one edge of the dressing to a centrally positioned aperture which is sized and shaped to receive and accommodate the cannula's connector. The existence of such slits substantially compromise the peripheral integrity of the dressing, thus increasing the risk of infection. The presence of a slit extending to the periphery of the dressing further adversely affects the resistance provided by it against unwanted pulling or pushing movement of the cannula.

Therefore known dressings for securing a cannula in position on a patient suffer from several disadvantages.

OBJECTS OF THE INVENTION

It is an object of the present invention to alleviate the drawbacks of prior art dressings by providing a dressing which allows improved securing of a cannula to a patient, and which minimizes the risk of infection.

Another object of the present invention is to provide a dressing which reduces the incidence of torn or damaged veins.

Yet another particular object of the present invention is to provide a dressing for catheterization procedures which is easy to use and economical to produce.

SUMMARY OF THE INVENTION

According to a first aspect of the present invention, there is provided a two-part overlapping dressing for securing a cannula on a skin surface of a patient, said dressing comprising: a first flexible adhesive sheet provided with an opening spaced from all peripheral edges of the first sheet; and a second flexible adhesive sheet; wherein
the opening in the first sheet comprises a slit, one end of which terminates in an enlarged aperture; and
the second sheet is dimensioned such that, when it is aligned with and adhered against the first sheet in use, it is capable of overlapping the full length of the slit so as to reduce the opening to the size of the enlarged aperture.

Optionally, a peripheral edge of the second sheet is provided with an indentation shaped and dimensioned such that, when the second sheet is aligned with and adhered against the first sheet, the indentation complements and delineates the enlarged aperture.

Optionally, the first sheet is symmetrical about a central longitudinal axis thereof and the slit extends along the axis.

Preferably, the length of the opening is less than 50% of the length of the first sheet when measured along its central longitudinal axis.

Optionally, the second sheet is symmetrical about a central longitudinal axis thereof and the indentation is formed about the axis where it meets a peripheral edge of the sheet.

Optionally, a surface of the first sheet comprises four separate release sheets which are releasable to expose four corresponding adhesive regions.

Optionally, one release sheet is arranged at the distal end of the first sheet, opposite the enlarged aperture, over a distal adhesive region.

Optionally, one release sheet is arranged at the proximal end of the first sheet, proximate the enlarged aperture, over a proximal adhesive region.

Optionally, the distally and proximally arranged release sheets partially surround the slit and enlarged aperture respectively.

Optionally, two central release sheets are arranged symmetrically either side of the opening over two corresponding central adhesive regions of the first sheet.

Optionally, each of the two central release sheets extend longitudinally along at least part of the length of the opening and laterally across the width of the first sheet between its lateral peripheral edges and the opposing longitudinal edges of the opening.

Optionally, distal and proximal edges of the two central release sheets are arranged such that they overlap the proximal and distal extents of the distal and proximal release sheets respectively.

Optionally, the distal, proximal and two central adhesive regions cumulatively cover the full surface area of the first sheet.

Optionally, the distal and proximal release sheets are folded to provide graspable tabs facilitating their release from their respective adhesive regions.

Optionally, a surface of the second flexible adhesive sheet comprises three separate release sheets which are releasable to expose three corresponding adhesive regions.

Optionally, two lateral release sheets are arranged symmetrically either side of the indentation over two corresponding symmetrical adhesive regions of the second sheet.

Optionally, a central release sheet is arranged along the central longitudinal axis over a corresponding central adhesive region of the second sheet.

Optionally, lateral edges of the central release sheet are arranged such that they overlap the inwardly opposing extents of the lateral release sheets respectively.

Optionally, the lateral and central adhesive regions cover the full surface area of the second sheet.

Optionally, the lateral release sheets are folded to provide graspable tabs facilitating their release from their respective adhesive regions.

Optionally, the release sheets arranged on the first and second sheets are provided with a visually discernable notation system to facilitate their correct sequential removal.

Optionally, the enlarged aperture is obround in shape so as to correspond with the outline of a part of a cannula.

Optionally, the indentation is semi-obround in shape and dimensioned to match the obround shape of the enlarged aperture.

According to a second aspect of the present invention, there is provided a method of securing a cannula to a patient by applying the dressing as defined by the first aspect.

BRIEF DESCRIPTION OF THE DRAWINGS

An embodiment of the present invention will now be described by way of example only with reference to the accompanying drawings in which:

Referring now to FIGS. 1a and 1b, there is shown a two-part overlapping dressing for securing a connector part of a cannula on the skin surface of a patient (as shown in FIG. 4). The dressing comprises first and second flexible adhesive sheets (10, 12). The first flexible adhesive sheet (10) is symmetrical about its central longitudinal axis (14). An opening (16) comprising a narrow slit portion (18) extends along the axis (14) and terminates at its proximal end in an enlarged aperture (20), i.e. the slit and the enlarged aperture are contiguous. The opening is situated within the body of the first sheet (10) and no part thereof extends to any of its peripheral edges.

Figure 1A:
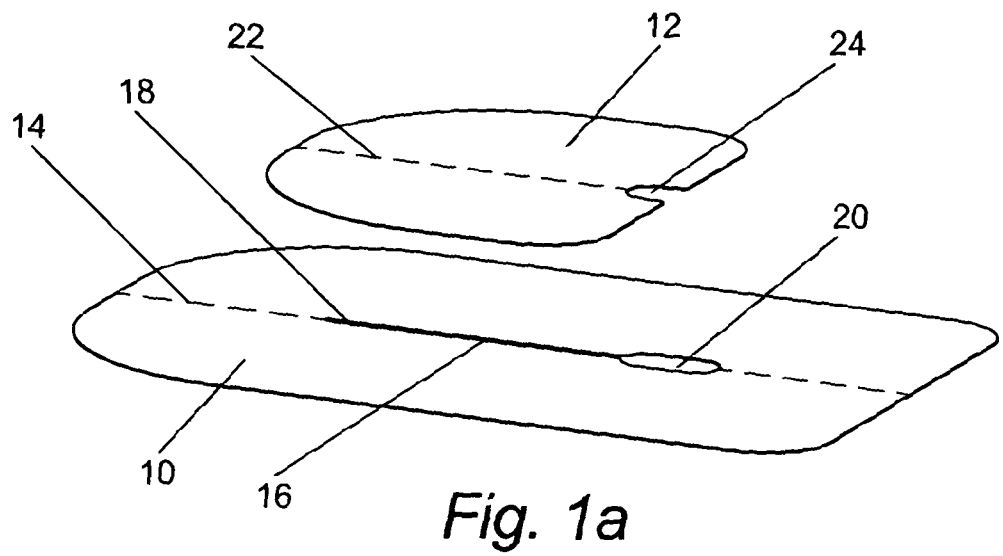
FIG. 1a is a perspective view of the first and second flexible adhesive sheets of the two-part dressing.
Figure 1B:
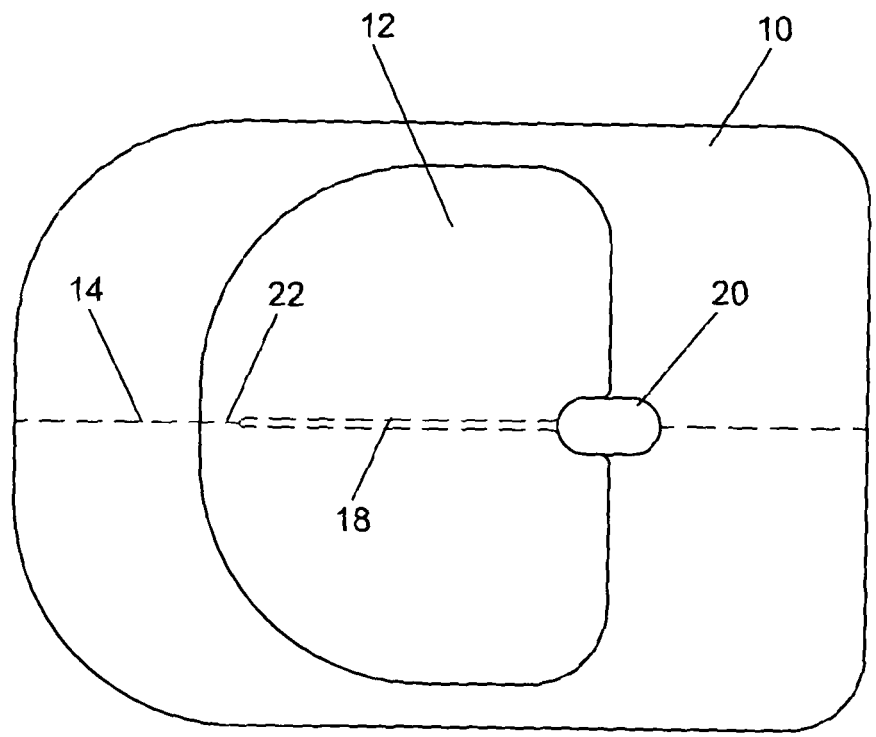
FIG. 1b is a top plan view of the second flexible adhesive sheet adhered in position over the underlying first flexible adhesive sheet.

In the particular embodiment shown in the figures, the first sheet is generally rectangular in shape with rounded corners. The two distal corners have a larger radius of curvature than the two proximal corners. The length of the opening (16) is approximately 49 mm which represents 37% of the length of the first sheet (99 mm) when measured along its central longitudinal axis. The slit portion (18) of the opening (16) is approximately 37 mm in length and 2 mm in width. A thin slit is preferred since such an arrangement maximises the adhesive surface around the injection site to be covered by the dressing. The enlarged aperture (20) of the opening (16) is generally obround in shape (i.e. its shape consists of two semi-circles connected by parallel straight lines tangent to their endpoints) and is approximately 12 mm in length and 6.5 mm in width. However, it will be appreciated that the particular size and shape of the internal aperture (20) will be determined by reference to the shape of the particular cannula part to be encircled by the edges of the opening (16). Based on standard cannulae currently in use in healthcare settings in United Kingdom, the enlarged aperture (20) is generally obround or oval in shape.

The first sheet has a width of approximately 70 mm. No part of the opening (16) is less than 24 mm from a peripheral edge of the first sheet (10). It will be appreciated that the general external dimensions of the dressing may be varied depending upon the particular part of a patient's body to which it is to be applied. In the illustrated example (see FIG. 4) the dressing is designed to be secured to the back of a patient's hand.

The second sheet (12) is also generally rectangular in shape with rounded corners and has an approximate length of 49 mm—i.e. equal to the length of the opening (16) of the first sheet—and has an approximate width of 60 mm. The two distal corners also have a larger radius of curvature than the two proximal corners. The second sheet (12) is symmetrical about a central longitudinal axis (22) thereof and an indentation (24) is formed about the axis (22) where it meets a proximal peripheral edge of the second sheet (12). The indentation (24) is shaped and dimensioned so as to match or complement the generally obround shape of the enlarged aperture (20) of the first sheet (10), i.e. the width of the indentation (24) is generally the same as the width of the enlarged aperture (20) at 6.5 mm, and the maximum inward extent or depth of the indentation is approximately half of the length of the enlarged aperture (20) at 6 mm.

In one example, the flexible material of the first and second flexible adhesive sheets (10, 12) may be a transparent material which is moisture permeable to avoid maceration of the skin. The vapour permeability of the dressing may be 2200 to 2600 $gm^{-2} 24\ h^{-1}$. Its thickness may fall within the range of 20 to 200 microns, and more preferably 25 to 35 microns and its weight may fall within the range 25 to 35 $gm^{-2}$. Suitable materials for the flexible sheet can be chosen in the group consisting of hydrophilic polymers such as hydrophilic polyurethane, polyether or polyester polyurethane, elastomeric polyether polyester, polyether polyamide, cellulose material etc.

Figure 2:
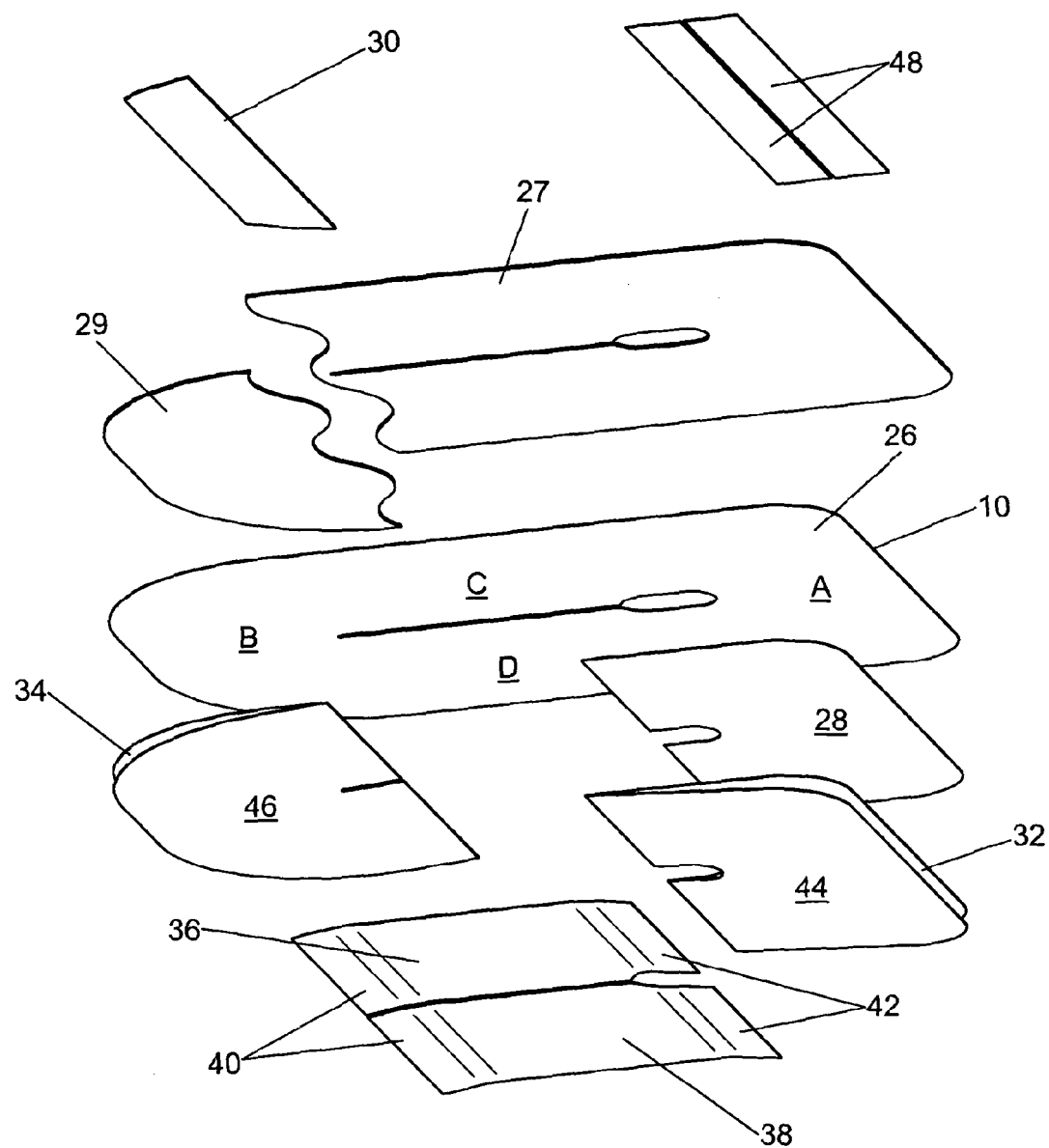
FIG. 2 is an exploded perspective view from beneath showing the individual components of the first flexible adhesive sheet of the two-part dressing.

FIG. 2 shows a bottom surface (26) of the first sheet (10) and is exploded to show its component parts and the positional arrangement of release sheets releasable to expose adhesive regions A-D on the bottom surface (26).

A soft non-woven mico-perforated pad (28) is adhered to the proximal end of the bottom surface (26) of the first sheet (10) and extends longitudinally from its proximal edge part of the way alongside the enlarged aperture (20). The pad (28) may be made from a nonwoven laminated absorbent material. In one example, the weight of the pad may be 106 gm$^{-2}$+/−15%, its absorption capacity may be 550%; it may comprise 270 parts per million +/−20% of silver; and it can be easily wiped clean from, for example, serum or blood. The outwardly facing surface of the pad (28) is provided with an adhesive for securing that part of the first sheet (10) to the skin of a patient. Therefore, the outwardly facing surface of the pad (28) defines adhesive region A mentioned above.

The first sheet (10) comprises four separate underlying release sheets (32, 34, 36, 38) which are releasable to expose four corresponding and adjoining adhesive regions (A, B, C, D) on its bottom surface. In one example, the weight of the underlying release sheets may fall within the range 67 to 77 gm$^{-2}$. In reverse order of removal in use, release sheet (32) covers adhesive region A at the proximal end of the first sheet (10). The part of the release sheet (32) which is temporarily adhered to adhesive region A is shaped and dimensioned to match the underlying pad (28). Release sheet (34) covers adhesive region B at the distal end of the first sheet (10). The part of the release sheet (34) which is temporarily adhered to adhesive region B is shaped and dimensioned so as to extend longitudinally from the distal edge of sheet (10) part of the way alongside the slit (18). Release sheets (32, 34) are spaced to define two symmetrical central adhesive regions C and D arranged laterally either side of the remainder of the opening (16). The two symmetrical central adhesive regions C and D are temporarily covered by release sheets (36, 38) respectively.

The distal and proximal edges of the central release sheets (36, 38) are arranged such that they overlap the proximal and distal extents of release sheets (32, 34) respectively. The overlapping distal and proximal edges of the central release sheets (36, 38) are not adhered to the underlying release sheets (32, 34) so as to define graspable tabs (40, 42) to facilitate removal to expose adhesive regions C and D. Release sheets (32, 34) are folded in half such that the halves thereof which are not temporarily adhered to adhesive regions A and B define graspable tabs (44, 46) to facilitate removal to expose those regions.

The first sheet (10) also comprises two separable overlying release sheets (27, 29) which are releasable to expose its top surface. In one example, the overlying release sheets (27, 29)—which may be paper-based or made from a polythene material—are preferably lightweight so as to promote flexibility of the laminated dressing once it has been attached to a patient's skin. A writable panel or label (30) is provided on the top surface of overlying release sheet (29) and may be removed and reapplied to the first sheet (10) and used to record patient-specific information. Two coated paper or polyamide adhesive strips (48) are releasably adhered—e.g. using DURO-TAK H1540 adhesive—on the top surface of the other overlying release sheet (27). The adhesive strips (48) may be used to initially secure the wings of a cannula connector (see FIG. 4) to the skin surface of a patient to maintain it sufficiently securely during the subsequent application of the two-part dressing. Optionally, the adhesive may be of a type that permits the strips (48) be peeled off and re-applied multiple times. The strips (48) can thus be re-positioned onto the patient if needed. Also the strips can be temporarily secured onto a part of the dressing so they are conveniently available for use.

Figure 3:
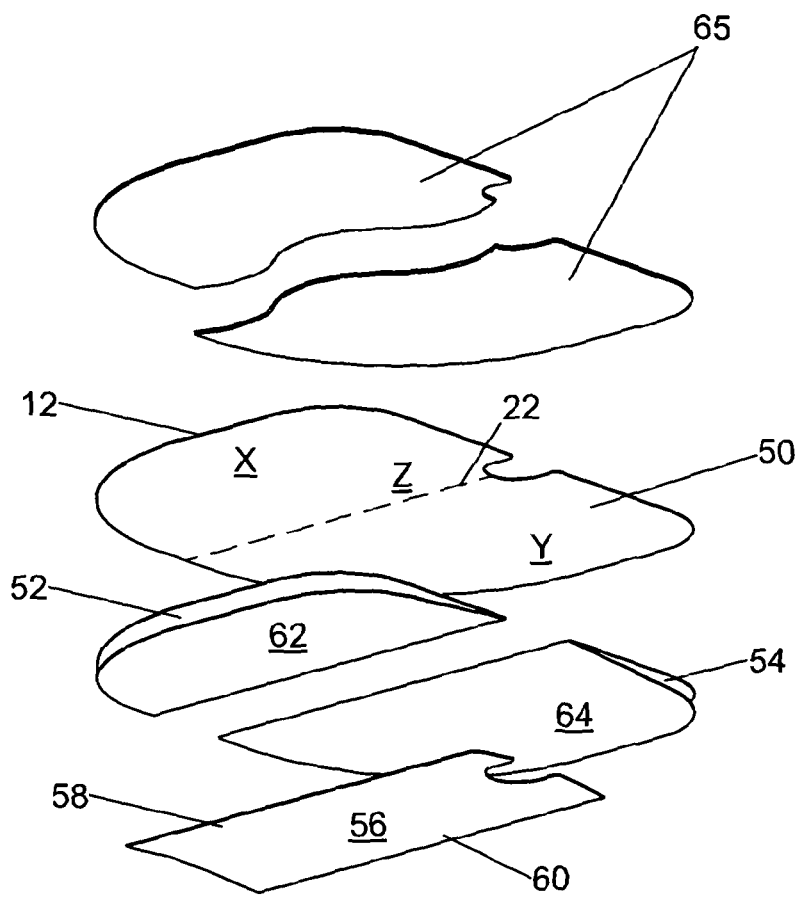
FIG. 3 is an exploded perspective view from beneath showing the individual components of the second flexible adhesive sheet of the two-part dressing.

FIG. 3 shows a bottom surface (50) of the second sheet (12) and is exploded to show its component parts and the positional arrangement of underlying and overlying (65) release sheets. The second sheet (12) comprises three separate underlying release sheets (52, 54, 56) which are releasable to expose three corresponding and adjoining adhesive regions (X, Y, Z) on its bottom surface (50). In reverse order of removal in use, release sheets (52, 54) cover adhesive regions X and Y respectively laterally of the central longitudinal axis (22) of the second sheet (12). The part of the release sheets (52, 54) which are temporarily adhered to adhesive regions X and Y are shaped and dimensioned to extend laterally, either side of the indentation (24). Release sheets (52, 54) are spaced to define a central adhesive region Z arranged about the central longitudinal axis (22) between the indentation (24) and the opposite peripheral edge of the second sheet (12). The central adhesive region Z is temporarily covered by release sheets (56).

The lateral edges of the central release sheet (56) are arranged such that they overlap the inwardly opposing extents of the lateral release sheets (52, 54) respectively. The overlapping lateral edges of the central release sheet (56) are not adhered to the underlying release sheets (52, 54) so as to define graspable tabs (58, 60) to facilitate removal to expose adhesive region Z. Release sheets (52, 54) are folded in half such that the halves thereof which are not temporarily adhered to adhesive regions X and Y define graspable tabs (62, 64) to facilitate removal to expose those regions.

Suitable pressure sensitive adhesive formulations for the adhesive regions A, B, C, D, X, Y and Z are widely available and may comprise at least one adhesive material selected from: hydroabietic acid, glycerol ester thereof, wood rosin derivatives, dodecyl maleamic acid, octadodecyl maleamic acid, tetrahydrofurfuryl, acrylate polymers such as p-tertbutylphenol formaldehyde resin and epoxy resins etc; in combination with other additives, such as an antioxidant (e.g. 2,5-di(tertiary-amyl)hydroquinone) or a preservative (e.g. diethyldithiocarbamate). In one embodiment, the adhesive used is a hot melt pressure adhesive sold under the Trade Mark DURO-TAK H1540 by National Starch & Chemical GmbH, Kalkarer Str. 81, 47533 Kleve Germany. In another example, the adhesive is an acrylic based solvent having the following characteristics: Adhesion Power=7 to 13 N/25 mm; Loop Tack=3 to 7 N/25 mm; Vapour Permeability=1600 to 2400 gm$^{-2}$ 24 h$^{-1}$. An antibacterial agent such as chlorhexidine or a silver oxide compound may be combined to the adhesive material in a proportion of 1 to 10%, preferably 5%, by weight of the adhesive.

Underlying release sheet materials include papers, silicon coated papers, polymeric films, such as silicone coated polyethylene, and woven and non-woven fabric of the type conventionally used in dressings. The release sheets can be conveniently printed with sequential numbering or lettering to assist the user in following the most practical sequence for their removal, and hence to facilitate the correct application of the dressing onto a patient.

The two-part dressing is of course preferably sterile and provided in a protective sealed wrapper made of, e.g. a coated paper and/or plastic and/or aluminium. Sterilisation of the dressing can be carried out by known methods such as ethylene oxide or, electron or gamma radiations. The use of ethylene oxide is preferred.

FIGS. 4 to 11 show the sequence of steps required to secure a cannula to the skin surface of a patient.

Figure 4:
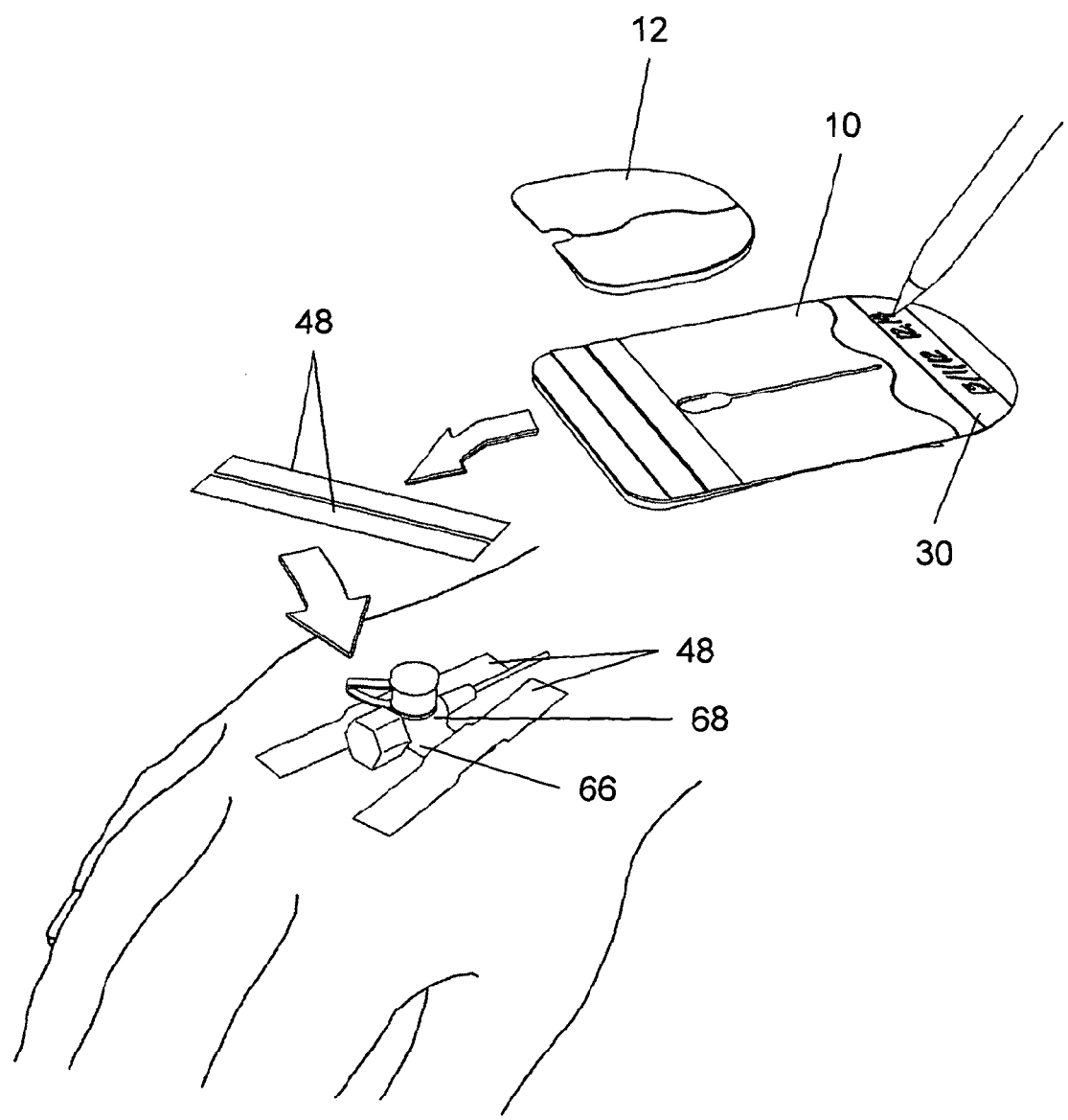
FIG. 4 is a perspective view of a two-part dressing showing the removal of adhesive strips for securing a cannula to the hand of a patient.

FIG. 4 is a perspective view of the two-part dressing showing how the adhesive strips (48) can be removed from the top proximal surface of the overlying release sheet (27) of the first sheet (10) and used to initially secure the wings (66) of a cannula's connector portion (68) to the hand of a patient. This step ensures that the cannula is kept sufficiently stable during the subsequent procedure for securing the two-part dressing over and around the cannula. Before the first sheet (10) is adhered to the patient, its writable panel or label (30) used to record any patient-specific information that may be required.

Figure 5:
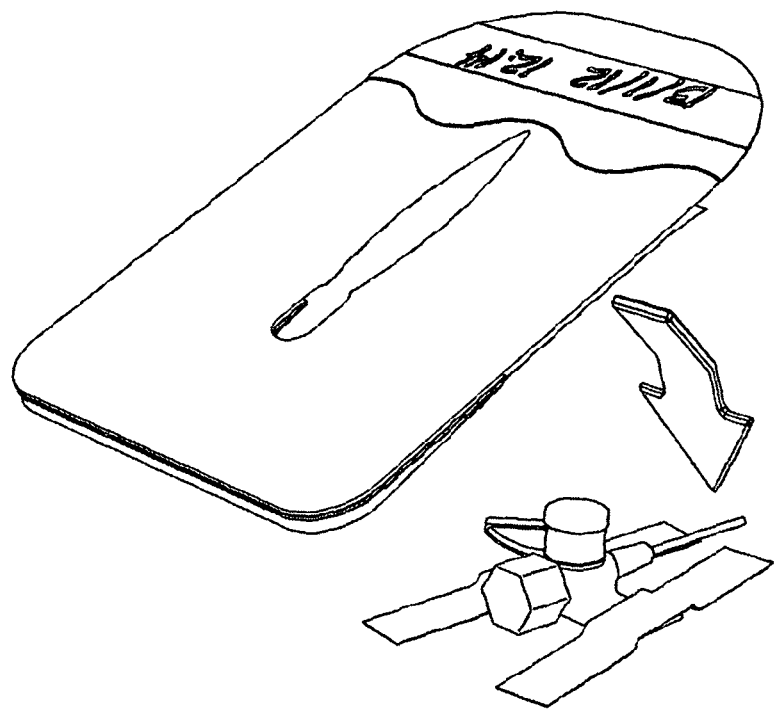
FIG. 5 is a perspective view of the dressing showing the lowering of its first flexible adhesive sheet towards the body portion of a cannula.
Figure 6:
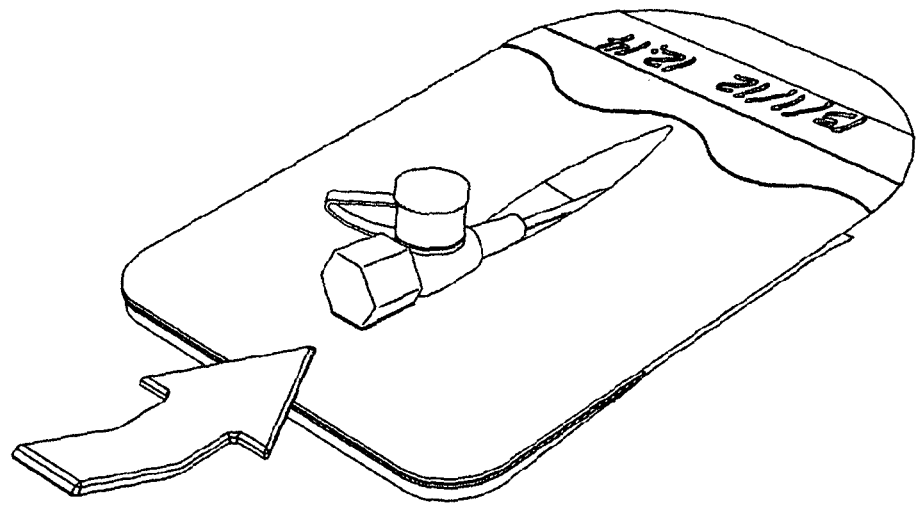
FIG. 6 is a perspective view of the dressing showing the application of its first flexible adhesive sheet over the body portion of a cannula.

FIGS. 5 and 6 show the steps of placing the first sheet (10) over the cannula such that its connector portion (68) extends through the opening (16) and the first sheet overlaps the cannula's wings (66). The pliability of the first sheet (10), the length of the slit (18) and the presence of the enlarged aperture (20) facilitate the passage of the connector portion (68) through the opening (16). The slit (18) is then generally aligned with the longitudinal axis of the cannula and moved distally in the direction of the arrow in FIG. 6 until the proximal edge of the enlarged aperture (20) abuts the proximal edge of the connector portion (68) and it can move no further.

Figure 7:
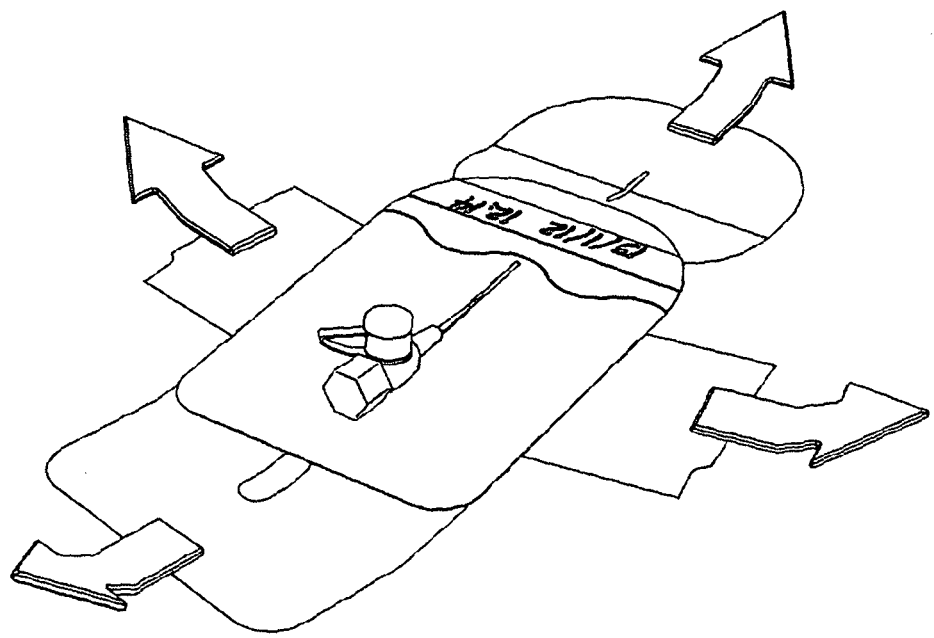
FIG. 7 is a perspective view of the dressing showing the removal of the central, distal and proximal release sheets from the first flexible adhesive sheet.

FIG. 7 shows the step of removing the central release sheets (36, 38) from the bottom surface (26) of the first sheet (10) in a lateral direction to expose the aforementioned adhesive regions C and D. Such removal may be facilitated by the adhesive-free graspable tabs (40, 42) provided at opposite ends of the release sheets (36, 38). As the adhesive regions are exposed, downward pressure can be applied to secure the central portion of the first sheet (10) to the skin surface of a patient, and to the connector wings (66) if present.

FIG. 7 also shows the step of removing the distal release sheet (34) from the bottom surface (26) of the first sheet (10) in a distal direction to expose the aforementioned adhesive region B. Such removal may be facilitated by the adhesive-free graspable tab (46). As the adhesive region B is exposed, downward pressure can be applied to secure the distal portion of the first sheet (10) to the skin surface of a patient.

Finally, FIG. 7 also shows the step of removing the proximal release sheet (32) from the bottom surface (26) of the first sheet (10) in a proximal direction to expose the aforementioned adhesive region A. Such removal may be facilitated by the adhesive-free graspable tab (44). As the adhesive region A is exposed, downward pressure can be applied to secure the remaining proximal portion of the first sheet (10) and its aforementioned pad (28) to the skin surface of a patient. In so doing, the entire bottom surface (26) of the first sheet (10) is adhered to the skin surface of a patient.

Figure 8:
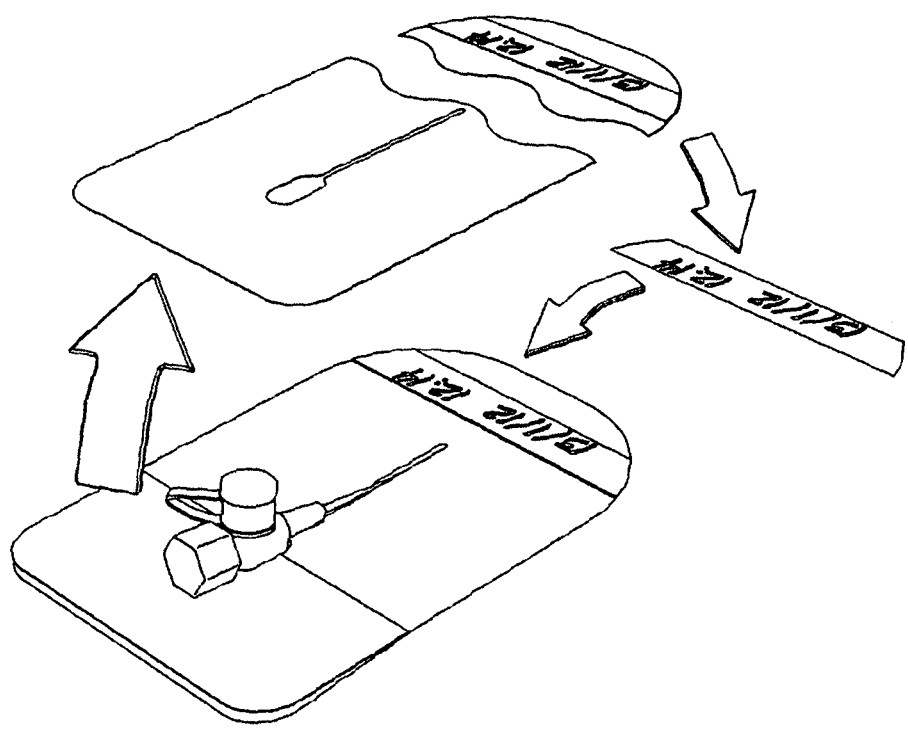
FIG. 8 is a perspective view of the dressing showing the removal of a writeable panel from an overlying release sheet of the first flexible adhesive sheet.

FIG. 8 shows the step of removing the overlying release sheets (27, 29) from the top surface of the first sheet (10). In doing so, only the thin transparent material of the first sheet (10) and the micro-perforated pad (28) remain on the patient's skin. The writable panel or label (30) may be removed from the top surface of the overlying release sheet (29) and reapplied to the first sheet (10) so as to display any relevant patient-specific information.

Figure 9:
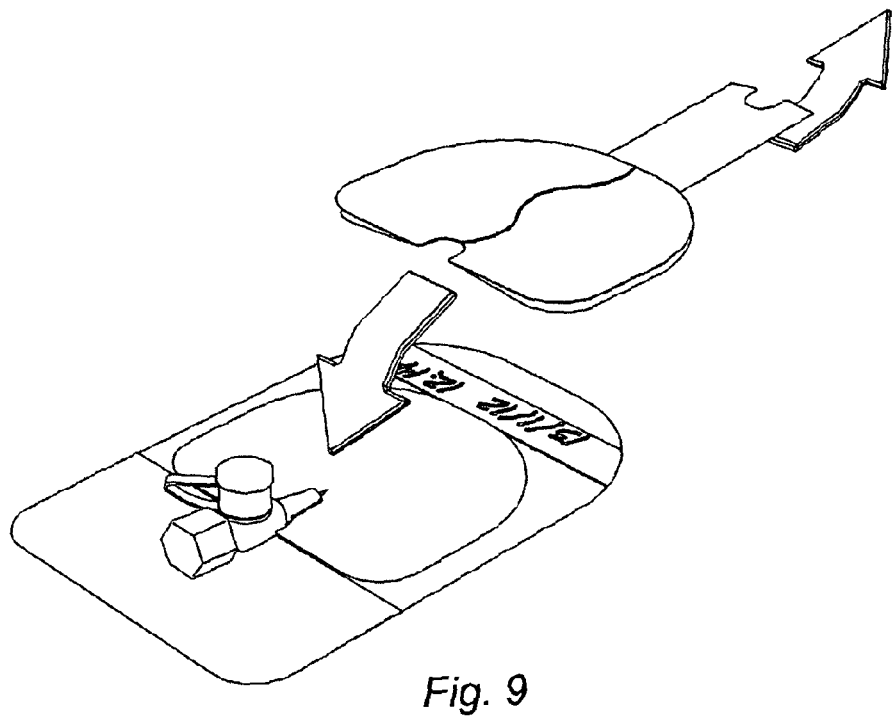
FIG. 9 is a perspective view of the dressing showing the removal of the central release sheet from its second flexible adhesive sheet and its application over the first flexible adhesive sheet.

FIG. 9 shows the step of removing the central release sheet (56) from the bottom surface (50) of the second sheet (12) in a longitudinal direction to expose the aforementioned adhesive region Z. Such removal may be facilitated by the adhesive-free graspable tabs (58, 60) provided at opposite longitudinal edges of the release sheet (56). As the adhesive region Z is exposed, downward pressure can be applied to secure the central portion of the second sheet (12) to the underlying first sheet (10) over its slit (18). Before doing so, the central longitudinal axis (22) of the second sheet is manually aligned with, and superimposed over, the central longitudinal axis (14) of the first sheet (10). The second sheet (12) is then moved proximally in the direction of the arrow until the innermost edge of the indentation (24) abuts the proximal edge of the connector portion (68) and it can move no further. In doing so, the indentation (24) complements and completes the enlarged aperture (20) and together they delineate the edges of a reduced sized opening (16) which closely abuts the entire perimeter of the cannula's connector portion (68) to secure it firmly in position on the skin surface of a patient.

Figure 10:
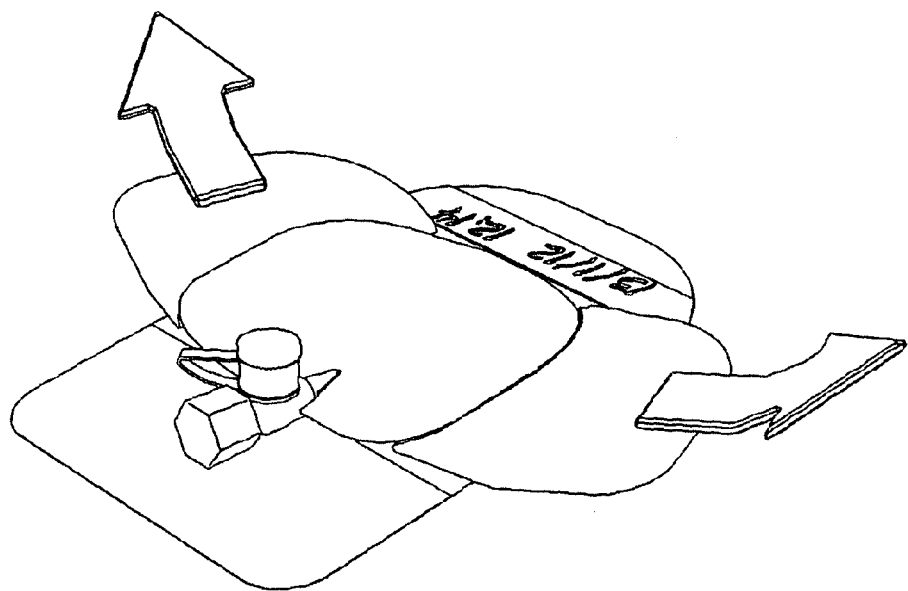
FIG. 10 is a perspective view of the dressing showing the removal of the lateral release sheets from the second flexible adhesive sheet.

FIG. 10 shows the step of removing the lateral release sheets (52, 54) from the bottom surface (50) of the second sheet (12) in lateral directions to expose the aforementioned adhesive regions X and Y. Such removal may be facilitated by the adhesive-free graspable tabs (62, 64). As the adhesive regions are exposed, downward pressure can be applied to secure the remaining lateral portions of the second sheet (12) to the underlying first sheet (10).

Figure 11:
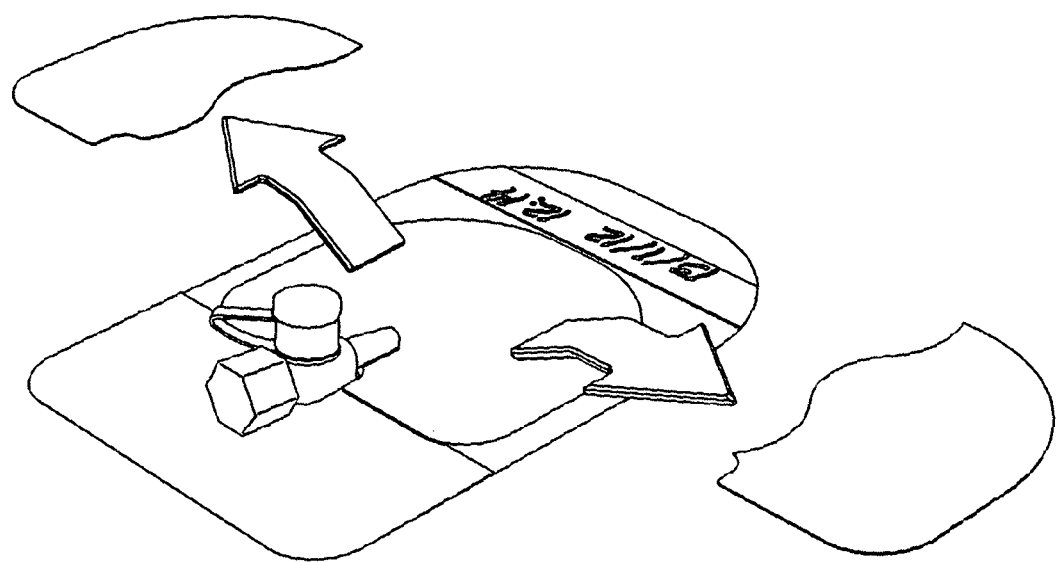
FIG. 11 is a perspective view of the dressing showing the removal of overlying release sheets of the second flexible adhesive sheet.

Finally, FIG. 11 shows the final step of removing the separable overlying release sheet portions (65) from the top surface of the second sheet (12) so as to promote flexibility of the laminated dressing once both its parts have been attached to a patient's skin.

The two-part dressing of the type described above provided numerous advantages over prior art dressings. For example, the absence of slits or indentations in the outer periphery of the first sheet (10) ensures that it maintains its structural integrity when adhered to a patient's skin and forms a tight and, importantly, continuous seal around the connector portion (68) of a cannula. The absence of any gaps or interruptions in the first sheet (10) greatly reduces the likelihood of infection at the site of the cannula's connector portion (68) by eliminating infection pathways leading to a dressing's internal opening.

The presence of multiple underlying release sheets (seven in the illustrated example) eases the process of applying the first and second sheets (10, 12) of the dressing to a patient. Not only is it easier for a medical practitioner to attach parts of the dressing in a sequential manner, but the division of the adhesive surface of the first and second sheets (10, 12) facilitates the prioritisation in terms of the order in which those parts are attached so as to minimise movement of the cannula after its insertion into the patient's body. A further advantage of the underlying release sheets is that the process of applying the dressing can be performed without the clinician physically contacting any of the adhesive regions A-D and X-Z.

It will be understood that the terms distal and proximal are used throughout the above description in a non limiting manner. In the illustrated embodiment, the terms distal is used to designate the direction in which the cannula is inserted into the body, whilst the term proximal designates the opposite direction. One skilled in the art will appreciate that the dressing of the invention may be adapted in terms of its overall shape and dimensions for a cannula being positioned at other parts of the human or animal body.

The invention claimed is:

1. A two-part overlapping dressing for securing a cannula on a skin surface of a patient, said dressing comprising:

a first flexible adhesive sheet comprising a top surface and a bottom adhesive surface comprising a release sheet releasably adhered thereto, the first flexible adhesive sheet being provided with an opening spaced from all peripheral edges of the first flexible adhesive sheet;

a second flexible adhesive sheet comprising a top surface and a bottom adhesive surface;

wherein the opening in the first flexible adhesive sheet comprises a slit, one end of which terminates in an enlarged aperture;

wherein the second flexible adhesive sheet is adapted to be adhered at its bottom surface to the top surface of the first flexible adhesive sheet;

wherein the second flexible adhesive sheet has a length greater than a length of the slit and is dimensioned such that, when it is aligned with and adhered against the first flexible adhesive sheet in use, it is capable of overlapping a full length of the slit so as to reduce the opening to a size of the enlarged aperture; and wherein a peripheral edge of the second flexible adhesive sheet is provided with an indentation shaped and dimensioned such that, when the second flexible adhesive sheet is aligned with and adhered against the first flexible adhesive sheet, the indentation complements and delineates the enlarged aperture.

2. The two-part overlapping dressing as claimed in claim 1, wherein the first flexible adhesive sheet is symmetrical about a central longitudinal axis thereof and the slit extends along the axis.

3. The two-part overlapping dressing as claimed in claim 2, wherein a length of the opening is less than 50% of a length of the first flexible adhesive sheet when measured along its central longitudinal axis.

4. The two-part overlapping dressing as claimed in claim 1, wherein the second flexible adhesive sheet is symmetrical about a central longitudinal axis thereof and the indentation is formed about the axis where it meets a peripheral edge of the sheet.

5. The two-part overlapping dressing as claimed in claim 1, wherein a surface of the first flexible adhesive sheet comprises four separate release sheets which are releasable to expose four corresponding adhesive regions.

6. The two-part overlapping dressing as claimed in claim 5, wherein one release sheet is arranged at a distal end of the first flexible adhesive sheet, opposite the enlarged aperture, over a distal adhesive region.

7. The two-part overlapping dressing as claimed in claim 6, wherein the distally arranged release sheet and a proximally arranged release sheets partially surround the slit and enlarged aperture respectively.

8. The two-part overlapping dressing as claimed in claim 7, wherein the distal and proximal release sheets are folded to provide graspable tabs facilitating their release from their respective adhesive regions.

9. The two-part overlapping dressing as claimed in claim 5, wherein one release sheet is arranged at a proximal end of the first flexible adhesive sheet, proximate the enlarged aperture, over a proximal adhesive region.

10. The two-part overlapping dressing as claimed in claim 5, wherein two central release sheets are arranged symmetrically on either side of the opening over two corresponding central adhesive regions of the first flexible adhesive sheet.

11. The two-part overlapping dressing as claimed in claim 10, wherein each of the two central release sheets extend longitudinally along at least part of a length of the opening and laterally across a width of the first flexible adhesive sheet between its lateral peripheral edges and opposing longitudinal edges of the opening.

12. The two-part overlapping dressing as claimed in claim 10, wherein a distal release sheet is arranged at a distal end of the first flexible adhesive sheet, opposite the enlarged aperture, over a distal adhesive region, wherein a proximal release sheet is arranged at a proximal end of the first flexible adhesive sheet, proximate the enlarged aperture, over a proximal adhesive region, and wherein distal and proximal edges of the two central release sheets are arranged such that they overlap proximal and distal extents of the distal and proximal release sheets respectively.

13. The two-part overlapping dressing as claimed in claim 10, wherein a distal release sheet is arranged at a distal end of the first flexible adhesive sheet, opposite the enlarged aperture, over a distal adhesive region, wherein a proximal release sheet is arranged at a proximal end of the first flexible adhesive sheet, proximate the enlarged aperture, over a proximal adhesive region, and wherein the distal, proximal and two central adhesive regions cumulatively cover a full surface area of the first flexible adhesive sheet.

14. The two-part overlapping dressing as claimed in claim 5, wherein a surface of the second flexible adhesive sheet comprises release sheets, and wherein the release sheets arranged on the first and second flexible adhesive sheets are provided with a visually discernable notation system to facilitate their correct sequential removal.

15. The two-part overlapping dressing as claimed in claim 1, wherein a surface of the second flexible adhesive sheet comprises three separate release sheets which are releasable to expose three corresponding adhesive regions.

16. The two-part overlapping dressing as claimed in claim 15, wherein two lateral release sheets are arranged symmetrically either side of the indentation over two corresponding symmetrical lateral adhesive regions of the second flexible adhesive sheet.

17. The two-part overlapping dressing as claimed in claim 16, wherein a central release sheet is arranged along a central longitudinal axis over a corresponding central adhesive region of the second flexible adhesive sheet.

18. The two-part overlapping dressing as claimed in claim 17, wherein lateral edges of the central release sheet are arranged such that they overlap inwardly opposing extents of the lateral release sheets respectively.

19. The two-part overlapping dressing as claimed in claim 17, wherein the lateral and central adhesive regions cover a full surface area of the second flexible adhesive sheet.

20. The two-part overlapping dressing as claimed in claim 16, wherein the lateral release sheets are folded to provide graspable tabs facilitating their release from their respective adhesive regions.

21. The two-part overlapping dressing as claimed in claim 1, wherein the enlarged aperture is obround in shape so as to correspond with an outline of a part of a cannula.

22. The two-part overlapping dressing as claimed in claim 21, wherein the indentation is semi-obround in shape and dimensioned to match the obround shape of the enlarged aperture.

23. A method of securing a cannula to a patient by applying a dressing as defined by claim 1 to a skin surface of the patient.

* * * * *